United States Patent
Skufca

(10) Patent No.: US 9,895,497 B2
(45) Date of Patent: *Feb. 20, 2018

(54) METHOD FOR REDUCING LEACHABLES AND EXTRACTABLES IN SYRINGES

(71) Applicant: Hexal AG, Holzkirchen (DE)

(72) Inventor: Peter Skufca, Stockach (DE)

(73) Assignee: Hexal AG, Holzkirchen (DE)

( * ) Notice: Subject to any disclaimer, the term of this patent is extended or adjusted under 35 U.S.C. 154(b) by 699 days.

This patent is subject to a terminal disclaimer.

(21) Appl. No.: 14/276,084

(22) Filed: May 13, 2014

(65) Prior Publication Data

US 2014/0323986 A1 Oct. 30, 2014

Related U.S. Application Data

(63) Continuation of application No. 12/993,585, filed as application No. PCT/EP2009/056176 on May 20, 2009, now Pat. No. 8,720,165.

(30) Foreign Application Priority Data

May 20, 2008 (EP) .................................. 08156573

(51) Int. Cl.
- *A61M 5/34* (2006.01)
- *B65B 3/00* (2006.01)
- *B65B 55/14* (2006.01)

(52) U.S. Cl.
CPC ......... *A61M 5/349* (2013.01); *A61M 2207/00* (2013.01); *B65B 3/003* (2013.01); *B65B 55/14* (2013.01); *Y10T 156/10* (2015.01)

(58) Field of Classification Search
CPC ..................... B65B 55/00–55/19; B65B 3/003
(Continued)

(56) References Cited

U.S. PATENT DOCUMENTS 4,240,423 A * 12/1980 Akhavi ................... A61M 5/34
604/272
4,468,223 A * 8/1984 Minagawa .......... A61M 5/3202
604/199

(Continued)

FOREIGN PATENT DOCUMENTS

EP 0709105 5/1996
EP 1892005 2/2008

(Continued)

OTHER PUBLICATIONS

Henkel Europe, Technical Data Sheet of Loctite 3345, Oct. 2010 (regarded as Applicant Admitted Prior Art). downloaded on Dec. 8, 2016 from URL: https://tds.us.henkel.com/NA/UT/HNAUTTDS.nsf/web/6C59ABB26D7FC454882571870000D67C/$File/3345-EN.pdf.*

*Primary Examiner* — Hemant M Desai
*Assistant Examiner* — Valentin Neacsu
(74) *Attorney, Agent, or Firm* — Lewis Kohn & Walker LLP; David M. Kohn; Kari Moyer-Henry

(57) ABSTRACT

The present invention relates to a method of producing syringes. Said method comprises fixing a needle to a syringe body by use of an adhesive followed by subjecting the syringes thus obtained to heat treatment. The invention further relates to a method of reducing leachables and/or extractables in prefilled syringes, said method comprising heat treating pre-fabricated syringes at a temperature of at least 40° C. before filling.

7 Claims, 4 Drawing Sheets

Fixing needle to syringe body ▶ heat treatment under reduced pressure ▶ washing at elevated temperature ▶ siliconization ▶ sterilization ▶ filling Fixing needle to syringe body ▶ washing and air drying ▶ siliconization ▶ sterilization ▶ packaging ▶ heat treatment at 40°C or more ▶ filling

(58) Field of Classification Search
USPC .................... 53/425, 426, 440, 428; 604/240
See application file for complete search history.

(56) References Cited

U.S. PATENT DOCUMENTS

| | | | | |
|---|---|---|---|---|
| 4,581,024 | A * | 4/1986 | Swenson | A61M 5/343 604/240 |
| 4,704,130 | A * | 11/1987 | Gilding | A61F 2/062 264/41 |
| 6,250,052 | B1 | 6/2001 | Porfano et al. | |
| 8,234,769 | B2 | 8/2012 | Leidig | |
| 8,720,165 | B2 * | 5/2014 | Skufca | A61M 5/349 53/287 |
| 2002/0069616 | A1 | 6/2002 | Odell et al. | |
| 2002/0138042 | A1 * | 9/2002 | Llorach | A61M 5/343 604/187 |
| 2005/0075611 | A1 | 4/2005 | Hetzler et al. | |
| 2008/0006574 | A1 * | 1/2008 | Ramaswamy | B01D 67/0065 210/490 |
| 2008/0075900 | A1 * | 3/2008 | Hepworth | C08J 5/045 428/35.6 |
| 2008/0213460 | A1 * | 9/2008 | Benter | A61L 31/048 427/2.1 |
| 2008/0248086 | A1 * | 10/2008 | Asgari | A61L 27/446 424/426 |
| 2008/0287990 | A1 * | 11/2008 | Smit | D07B 1/025 606/228 |
| 2009/0209919 | A1 * | 8/2009 | Sakurai | A61M 5/284 604/192 |
| 2011/0077602 | A1 | 3/2011 | Yokota et al. | |
| 2011/0190711 | A1 * | 8/2011 | Skufca | A61M 5/349 604/240 |

FOREIGN PATENT DOCUMENTS

| | | | |
|---|---|---|---|
| GB | 1215435 | 12/1970 | |
| WO | WO 2006132176 A1 * | 12/2006 | ............ A61M 5/284 |

\* cited by examiner

Fixing needle to syringe body ▲ washing and air drying ▲ siliconization ▲ sterilization ▲ filling

Fig.1b

Fixing needle to syringe body ▲ heat treatment under reduced pressure ▲ washing at elevated temperature ▲ siliconization ▲ sterilization ▲ filling

Fig.1c

Fixing needle to syringe body ▲ washing and air drying ▲ siliconization ▲ sterilization ▲ packaging ▲ heat treatment at 40°C or more ▲ filling

METHOD FOR REDUCING LEACHABLES AND EXTRACTABLES IN SYRINGES

CROSS REFERENCES

This application is a continuation of U.S. patent application Ser. No. 12/993,585, filed Feb. 15, 2011, now U.S. Pat. No. 8,720,165, which claims priority under 35 U.S.C. 371 from International Patent Application No. PCT/EP2009/056176 filed May 19, 2009, which claims the benefit of priority from European Patent Application Serial No. 08156573.1 filed May 20, 2008, the entire contents of which are herein incorporated by reference.

DESCRIPTION

The present invention relates to a method of reducing leachables and/or extractables in syringes, especially pre-filled syringes, by heat treatment.

Leachables and extractables in container and container closure systems are a common problem when using drugs and biologics for analytical and medical purposes. Leachables and extractables are substances that are released from the surface of a container material and migrate to the products contained. As far as injectable dosage forms are concerned, for example, care must be taken to avoid leaching and extracting of undesired substances from vial or syringe materials into the drug vehicle, as leachables and extractables increase drug product contamination and may interact with the active ingredient causing inactivity or toxicity.

Syringes used for injecting drugs, such as pre-filled syringes for single use, are known in various forms. These syringes include a cylindrical syringe body made of glass or plastic with an injection needle attached thereto. Conventional processes for the manufacture of pre-filled syringes for single use provide syringe bodies with a first open end for a syringe piston and a second open end for securing an injection needle. After arranging the needle in the needle channel, the needle is fixed to the syringe body, typically by use of radiation-curable adhesives, for example photo-curing adhesives. Following curing, for example by UV-irradiation, the syringes are flushed several times for 1 to 3 sec with hot water at about 70° C. for cleaning. This is usually followed by siliconization and sterilization, for example ethylene oxide (ETO) sterilization. In a final step, the syringes are filled with the desired injectable product. The syringes thus obtained, however, have the disadvantage that leachables/extractables from the adhesive may migrate to the liquid vehicle. In syringes pre-filled with, for example, drug vehicles such as buffers, leachables/extractables derived from the adhesive can be observed in particular upon storage over long periods of time and at elevated temperatures.

In order to avoid contact of the syringe contents with the adhesive, EP-A-1 364 670 discloses a pre-filled syringe wherein the injection needle is clamped into the needle channel in the syringe body.

EP-A-1 818 069 discloses a method for producing pre-fillable syringes including a siliconization step. The syringes are subjected to heat treatment at a temperature of from 120° C. to 350° C. to fix the silicone applied on the syringe. The adhesives typically used for attachment of the injection needles to the syringe, however, cannot withstand high temperatures. In order to overcome this disadvantage, DE-A-2 939 180 discloses a combined ampoule injection syringe which comprises a needle-carrying connection piece which is assembled with the syringe body following siliconization. As the needle, however, is fixed with an adhesive, this still involves the risk of leachables and extractables migrating to the syringe contents.

The object of the present invention, therefore, was to provide syringes, in particular for medical use, with a reduced content of leachables/extractables.

This object has been achieved by the methods of producing syringes, said method comprising fixing a needle to a syringe body by use of an adhesive followed by subjecting the syringes thus obtained to heat treatment, reducing leachable and/or extractables in prefilled syringes, said method comprising heat treating prefabricated syringes at a temperature of at least 40° C. before filling and obtaining pre-filled syringes according to said methods. Specific embodiments of the methods of the invention are indicated in the dependent claims.

Thus, the present invention relates to a method of producing syringes, said method comprising fixing a needle to a syringe body by use of an adhesive followed by subjecting the syringe thus obtained to heat treatment.

It has surprisingly been found that leachables/extractables in pre-filled syringes can considerably be reduced within a short period of time if attachment of the needle with an adhesive is followed by heat treatment prior to further processing steps such as siliconization and sterilization.

The term "pre-filled syringe" as used herein is meant to include filled syringes or syringes ready for filling.

The terms "leachables" and "extractables" as used herein have the meaning common in the art. In particular, the term "leachables" means compounds that migrate, under intended storage conditions, from the contact surface of the syringe materials, in particular from the glass of the syringe body and/or from the adhesives used for needle attachment, to the syringe body, to the syringe contents, for example drug vehicles. The term "extractables" means compounds that can be extracted from the contact surface of the syringe materials under more aggressive conditions such as elevated temperature or extended contact time. Leachables/extractables released from the glass of the syringe bodies may be borates, and leachables/extractables released from adhesives may be components from the adhesives including, without being limited thereto, residual solvents, monomeric and polymeric components, additives such accelerators, and impurities. Leachables and extractables in adhesives may result from incomplete drying, from incomplete curing or from unreacted adhesive components present in excessive amounts.

In the course of the manufacturing method of the invention, an injection needle is fixed to the syringe body, usually a syringe body made of glass, by use of an adhesive. Adhesives used for attachment of injection needles to syringes are well known in the art. Suitable adhesives are fast-curing, in particular radiation curing adhesives, typically light- or photo-curing adhesives, such as acrylate-based adhesives, which can be cured by visible light or UV-light. Photo-curing adhesives are commercially available, for example under the trade name Loctite®, such as Loctite® 3345 (Henkel AG, Germany). Curing is carried out as indicated by the suppliers and usually is effected within a few seconds to some minutes.

Following needle attachment, the syringes thus obtained are subjected to heat treatment, i.e., they are heat treated before they are subjected to further processing steps such as siliconization, sterilization, packaging and/or filling. Heat treatment is carried out under conditions of temperature and pressure suitable to enhance release of leachables/extractables from the syringe, in particular of volatile substances. The heat treatment of the invention not only enhances release of substances contained in the glass material of the syringes and in the adhesives, but also enhances completion of polymerization of the adhesive. This accelerates formation and removal of potential leachables/extractables which otherwise would form only after filling the syringes and then cannot be removed any more. Early removal of these substances, therefore, results in medical products with increased purity and safety.

According to one embodiment of this method, heat treatment comprises heating the syringes to a temperature of at least about 40° C., preferably of at least about 50° C., and most preferably of at least about 60° C., under ambient pressure. Typically, the upper temperature for the heat treatment is limited by the thermal resistance of the syringe materials, in particular by the adhesive materials, and usually does not exceed about 140° C. Most preferably, heat treatment is carried out at a temperature of from about 60 to 120° C. or less. Heat treatment is carried out for a period of time suitable to enhance the release of leachables/extractables at a given temperature. Usually, if heat treatment is carried out at high temperatures, the time for heat treatment may be reduced. Typically, heat treatment is carried out for at least about 5 min, preferably for at least about 30 min, and most preferably for about 60 to 120 min.

According to a preferred embodiment of this method, heat treatment is carried out under reduced pressure. In this embodiment, syringes are typically pre-heated to the desired temperature at ambient pressure before applying reduced pressure. Heat treatment under reduced pressure results in accelerated release and removal of leachables and extractables from the syringe. Typically, the pressure is reduced to a pressure of about 400 mbar or less, preferably of about 40 mbar or less. For best results, heat treatment under reduced pressure is carried out for a time sufficient to effectively remove leachables and extractables released from the syringe at a given pressure, for example leachables and extractables released from the glass and/or from the adhesive surface. Typically, reduced pressure is applied for at least about 10 min following pre-heating the syringes to the desired temperature, but usually is applied for most of the heating. Advantageously, heat treatment under reduced pressure is carried out in a vacuum chamber.

Following heat treatment as described above, syringes may optionally be subjected to washing with water at elevated temperatures, for example hot water at a temperature of about 70° C. or more, followed by drying with hot dry air.

According to an alternative embodiment of this method of the invention, heat treatment of the syringes following needle attachment is carried out by washing the syringes with water at a temperature of at least about 80° C., preferably of at least about 90° C., most preferably of from about 95 to 100° C., preferably with steam. Preferably, washing comprises several washing steps, advantageously washings with water at various pH values (acidic, preferably down to a pH of about 2, alkaline, preferably up to a pH of about 10, or neutral) to remove leachables/extractables which are soluble in acidic, neutral and alkaline water. Typically, the last washing is carried out with neutral water, usually Water for Injection (WFI). Typically, syringes are washed with water or steam in the order acidic/neutral/alkaline/neutral. If desired, washings may be carried out by flushing the syringes with steam, for example 1 to 6 times flushing with steam for 1 to 10 seconds. Optionally, washing of the syringes with water can be preceded by a step of autoclaving the syringes under standard conditions. Washing is usually followed by drying with hot dry air.

The above conditions for washing can also be applied after syringes have been subjected to heat treatment at ambient or reduced pressure as described above.

Following heat treatment as described above, the syringes thus obtained can be further processed according to conventional methods well known in the art. This includes, for example, siliconization (see, e.g., EP-A-1 818 069), sterilization, for example ethylene oxide (ETO) sterilization in accordance with general standards (e.g., ISO 11135 and DIN EN 1422), providing syringes with further parts such as needle guards, packaging and filling.

The present invention also relates to a method of reducing leachables and/or extractables in prefilled syringes, wherein pre-fabricated syringes are heat treated at a temperature of at least about 40° C. prior to filling.

The term "pre-fabricated syringe" as used herein means syringes ready for filling, e.g., sterilized syringes.

Pre-fabricated syringes to be heat treated according to the invention may be packaged or may not be packaged. Advantageously, heat treatment of pre-fabricated syringes is carried out on packaged syringes to keep the syringes under sterile conditions. Heat treatment of pre-fabricated syringes may be carried out under ambient pressure or under reduced pressure at a temperature of at least about 40° C., preferably of at least about 50° C. When heat treating packaged syringes, the upper temperature limit is given by the thermal resistance of the package material and usually does not exceed about 100° C. Most preferably, heat treatment is carried out at a temperature of from about 50 to 80° C., for example at about 60 to 70° C. As above, heat treatment is carried out for a predetermined period of time sufficient to enhance the release of leachables/extractables at the given temperature. Usually, if heat treatment is carried out at high temperatures, heat treatment may be reduced. Heat treatment is usually carried out for at least 2 days, preferably for about 1 week, more preferably for about 1 to 3 weeks, and most preferably for about two weeks.

The present invention will be further illustrated with reference to the Examples and Figures below without being limited thereto.

BRIEF DESCRIPTION OF DRAWINGS

FIG. 1 schematically shows a conventional manufacturing process for syringes (FIG. 1a) and manufacturing processes involving heat treatment according to the invention (FIGS. 1b and c).

DETAILED DESCRIPTION OF THE INVENTION

FIG. 1 schematically shows a comparison between conventional methods of the prior art and specific embodiments of the methods of the invention. As will be seen from FIG. 1a, according to conventional methods, there are provided syringe bodies, usually made of glass, which have an opening for a piston at one end and an opening for receiving the injection needle at the opposite end. Injection needles are then attached by fixing the needle in the needle channel of the syringe body using an adhesive, such as a radiation-curing adhesive, for example an acrylate-based adhesive such as Loctite® 3345 (Henkel AG, Germany). Following curing of the adhesive, for example, by irradiation with UV-light, the syringes thus obtained are subjected to washing with hot water (usually 3 washings at about 70° C., 3×10 sec) followed by drying with hot sterilized air. The dry syringes are then subjected to siliconization with silicone oil, for example by spraying, and sterilized using, e.g., ethylene oxide (ETO) sterilization in accordance with known methods. The obtained syringes are packaged or filled with the desired product including closure of the syringes with a piston.

According to an embodiment of the method of the present invention shown in FIG. 1b, injection needles are attached to syringe bodies as described above. The syringes thus obtained are then subjected to heat treatment under reduced pressure. Heat treatment under reduced pressure is followed by washing with hot water and drying with hot dry air. The dry syringes are then subjected to siliconization and sterilization in accordance with conventional methods art and filled with the desired product.

According to a further method of the present invention shown in FIG. 1c, conventionally pre-fabricated syringes are packaged and heat treated by heating the packaged syringes to a temperature of from about 50 to 80° C., which temperature is preferably maintained for at least one week. The heat treated syringes can be subjected to further storage before filling, or they can immediately be filled with the desired product.

Example

Commercially available sterile syringes including injection needles fixed by an adhesive were unpacked. A first group consisting of 5 syringes was heated to a temperature of 80° C. and left at this temperature for one week. Subsequently, the syringes were filled with a phosphate buffer, pH 7.0, usually used in pharmaceutical industry and stored for 6 months at 25° C. A second group of 5 syringes, the control group, was left untreated but filled and stored in the same manner as the first group. A minute amount of the adhesive used for attachment of the injection needles to the syringes was dissolved in the same phosphate buffer for comparison.

Figure 2:
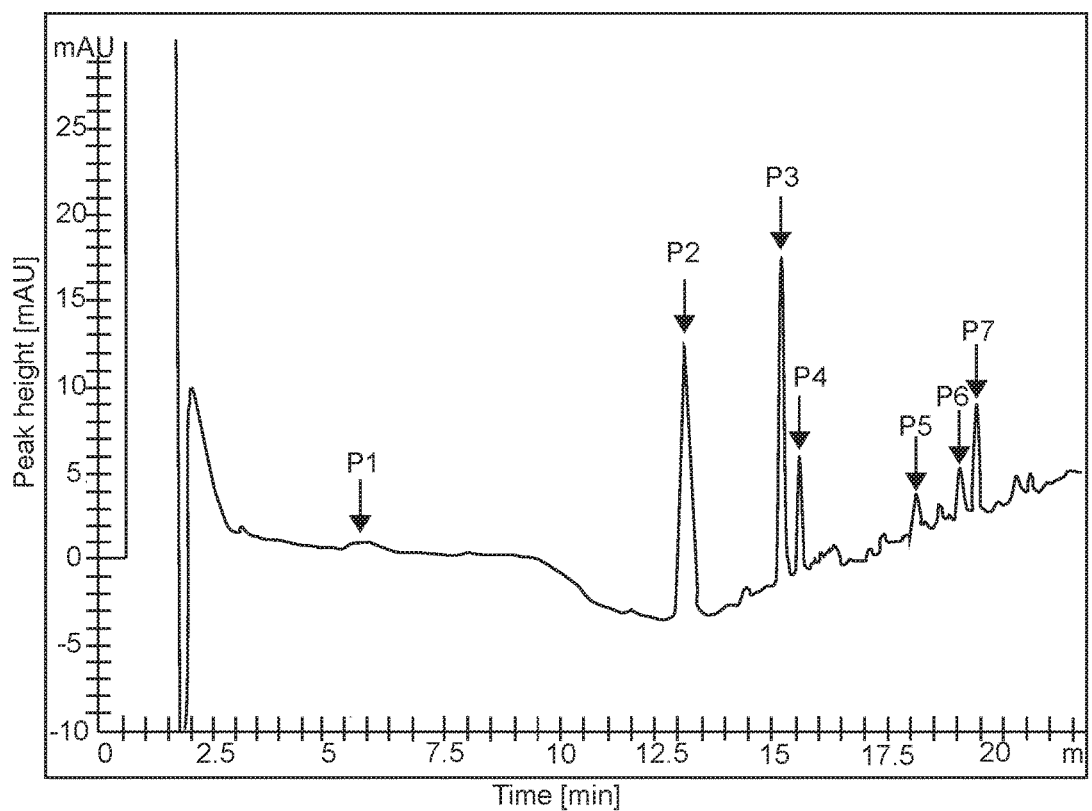
FIG. 2 shows a leachable/extractable profile of a commercially available, unpackaged syringe after 6 months of storage at 25° C. without prior heat treatment.
Figure 3:
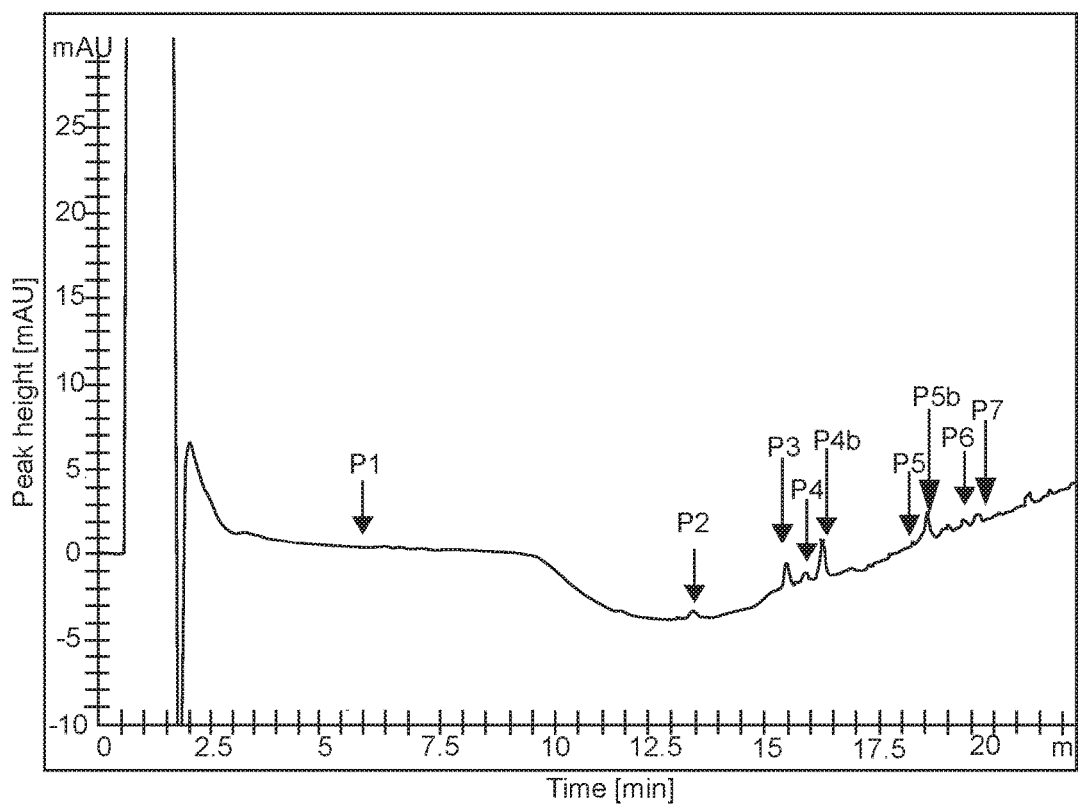
FIG. 3 shows a leachable/extractable profile of a commercially available, unpackaged syringe after 6 months of storage at 25° C. after heat treatment for 1 week at 80° C.
Figure 4:
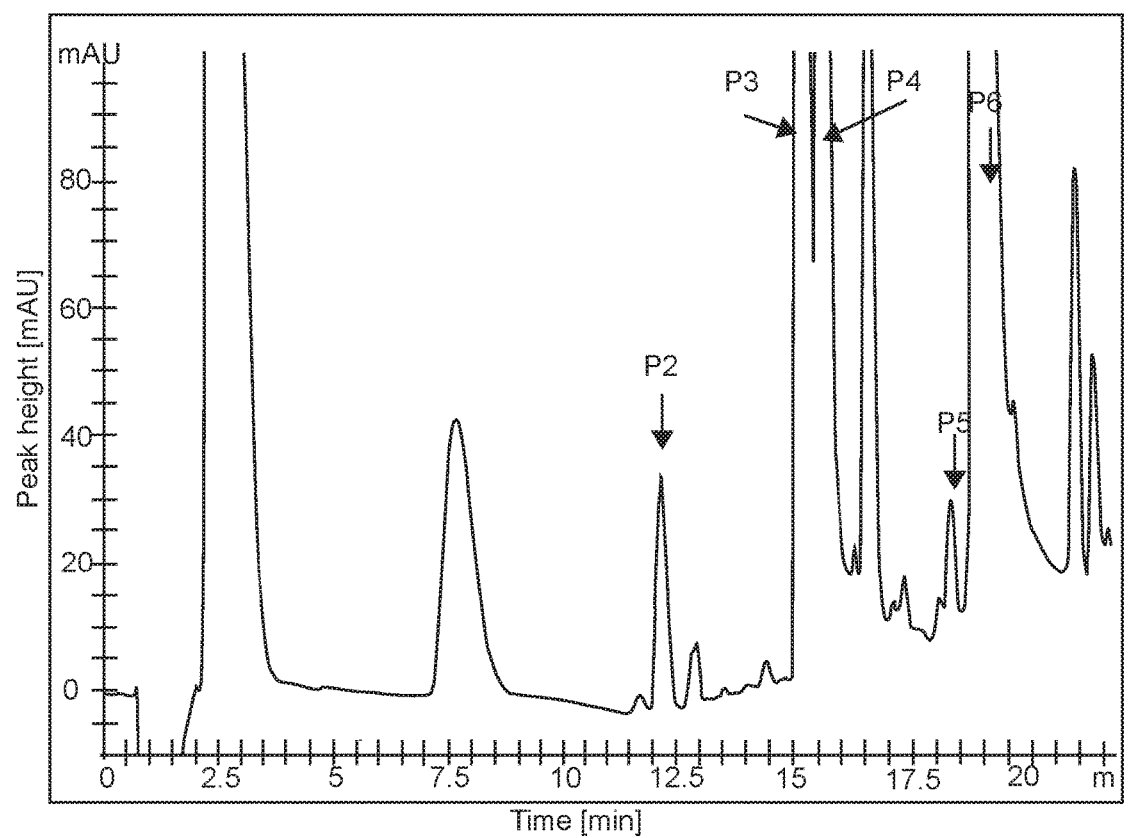
FIG. 4 shows a chromatograph of a commercially available adhesive used for fixing injection needles.

Following storage, the leachable/extractable content of the phosphate buffer of the two groups of syringes was tested by C18 RP-HPLC on an Agilent Series 1100 HPLC System using an acetonitrile gradient from 0 to 100% optimized for separation and detection of water soluble substances. The phosphate buffer with the dissolved adhesive was subjected to HPLC the same way as a further control. The results are shown in FIGS. 2 to 4 and in Table 1 below. FIG. 2 shows the chromatograph, the leachable/extractable profile, of the control without heat treatment, and FIG. 3 shows the leachable/extractable profile of the syringes after heat treatment. FIG. 4 shoes the chromatograph of the adhesive used for attachment of the injection needles to the syringes. Peaks are numbered in the order of appearance.

As may be seen from a comparison of FIGS. 2 and 4, peaks P2 to P6 which appear in the control group after 6 months of storage at 25° C. (FIG. 2) correspond to water soluble components present in the adhesive prior to polymerization (FIG. 4). Peaks P1 and P7 seen in FIG. 2 are products resulting from polymerization and, therefore, are not seen in the adhesive. In contrast, as may be seen from FIG. 3, the amount of leachables/extractables released into the phosphate buffer after heat treatment is much lower. While peaks P4b and P5b are additional peaks resulting from heat treatment of the syringes at 80° C., they represent negligible amounts compared to the reduction in other leachables/extractables.

The results are summarized in Table 1 below.

TABLE 1

| Peak number | Leachable/extractable peak area [mAU · s] | | Improvement [%] |
| --- | --- | --- | --- |
| | No Heat Treatment | Heat treatment | |
| P1* | 20.5 | n.a. | 100 |
| P2 | 235.0 | n.a. | 100 |
| P3 | 134.5 | n.a. | 100 |
| P4 | 55.1 | n.a. | 100 |
| P4b | n.a. | 16.4 | Additional peak |
| P5 | 19.2 | n.a. | 100 |
| P5b | n.a. | 15.2 | Additional peak |
| P6 | 24.9 | n.a. | 100 |
| P7* | 49.6 | n.a. | 100 |

*by products from polymerization;
n.a.: not analyzed (<10 mAU · s)
mAU: milli absorbance units The above results demonstrate that untreated syringes may release undesired amounts of leachables/extractables into liquid carriers contained in pre-filled syringes. The methods of the invention result in reduced leachable/extractable profiles of the medical products contained in the syringes and, consequently, in a higher safety and activity of these products due to a reduced toxicology and reduced interaction of leachables and extractables with the active ingredients. In addition, the method of the present invention allows a better reproducibility of the polymerization degree of the adhesive used for attaching the needles. The lower content of leachables/extractables in the syringes obtained according to the invention also results in a reduced risk when developing new products, in an accelerated development of new products, in less analytical efforts before filling and in enhanced proceedings before the health authorities.

The invention claimed is:

1. A method of reducing leachables and extractables released from an interior surface of syringe, wherein the syringe is unfilled, packaged, sterilized, and further ready for filling, said syringe having a needle fixed to a syringe body by use of a photo-curing adhesive, wherein reducing leachables and extractables comprises a step of:
    subjecting said unfilled packaged sterilized syringe to heat treatment, wherein the syringe is heated to a temperature of from 40° C. to 100° C., reducing the leachables and extractables released into an interior volume defined by the interior surface of the syringe.

2. The method of claim 1, wherein the syringe is heated to a temperature of from 50° C. to 80° C.

3. The method of claim 2, wherein the syringe is heated to a temperature of from 60° C. to 70° C.

4. The method of claim 1, wherein said heat treatment is carried out under a pressure of 400 mbar or less.

5. The method of claim 4, wherein the pressure is 40 mbar or less.

6. The method of claim 1, wherein said heat treatment is carried out for at least 1 week.

7. The method of claim 6, wherein said heat treatment is carried out for 1 to 3 weeks.

* * * * *

UNITED STATES PATENT AND TRADEMARK OFFICE
CERTIFICATE OF CORRECTION

| | |
|---|---|
| PATENT NO. | : 9,895,497 B2 |
| APPLICATION NO. | : 14/276084 |
| DATED | : February 20, 2018 |
| INVENTOR(S) | : Skufca |

It is certified that error appears in the above-identified patent and that said Letters Patent is hereby corrected as shown below:

In the Specification

Column 1, Line 10: the "19" should read "20"; and

Column 5, Line 23: between the word "methods" and the word "art" insert the phrase --in the--.

Signed and Sealed this
Seventeenth Day of April, 2018

Andrei Iancu
*Director of the United States Patent and Trademark Office*